US011090478B2

(12) United States Patent
Wegener et al.

(10) Patent No.: US 11,090,478 B2
(45) Date of Patent: Aug. 17, 2021

(54) SYSTEM AND METHOD OF STERILELY CONNECTING FLUID PATHWAYS

(71) Applicant: Fenwal, Inc., Lake Zurich, IL (US)

(72) Inventors: Christopher J. Wegener, Libertyville, IL (US); Mark Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/227,714

(22) Filed: Dec. 20, 2018

(65) Prior Publication Data

US 2019/0192844 A1    Jun. 27, 2019

Related U.S. Application Data

(60) Provisional application No. 62/608,995, filed on Dec. 21, 2017.

(51) Int. Cl.
*A61M 39/18*    (2006.01)
*B08B 7/00*    (2006.01)
(Continued)

(52) U.S. Cl.
CPC ............. *A61M 39/18* (2013.01); *A61L 2/04* (2013.01); *A61L 2/07* (2013.01); *A61L 2/081* (2013.01);
(Continued)

(58) Field of Classification Search
CPC .. A61M 39/18; A61M 39/1055; A61M 39/26; A61M 1/0209; A61M 39/105; A61M 1/025; A61M 2039/1033; A61M 2039/261; A61M 2039/263; A61M 2039/268; A61M 2039/1038; A61M 2039/167;
(Continued)

(56) References Cited

U.S. PATENT DOCUMENTS 5,194,145 A    3/1993   Schoendorfer
5,868,696 A    2/1999   Giesler et al.
(Continued)

FOREIGN PATENT DOCUMENTS

EP          3216487 A1    9/2017
JP    WO2013/153722 A1   10/2013
(Continued)

OTHER PUBLICATIONS

Terumo Translation relied on for rejection (Year: 2013).*
(Continued)

*Primary Examiner* — Sean E Conley
*Assistant Examiner* — Brendan A Hensel
(74) *Attorney, Agent, or Firm* — Cook Alex Ltd.

(57) ABSTRACT

A sterile tube connector for a fluid circuit system comprising a housing. A first opening is configured to receive a first length of tubing in communication with a first chamber. A second opening is configured for communicating with the first chamber when the tube connector is in an open configuration but not in a closed configuration. The second opening is configured to reversibly engage a third opening to form a second chamber. The third opening is configured for communicating with a second length of tubing. A first portion of the housing forming the first opening comprises a material at least partially permeable to a sterilization energy source for sterilizing contents of the second chamber.

12 Claims, 9 Drawing Sheets

(51) Int. Cl.
  *B08B 9/02* (2006.01)
  *A61L 2/10* (2006.01)
  *A61L 2/08* (2006.01)
  *A61L 2/04* (2006.01)
  *A61L 2/07* (2006.01)
  *A61M 1/02* (2006.01)
  *A61M 39/10* (2006.01)
  *B08B 9/027* (2006.01)
  *A61M 39/26* (2006.01)
  *A61M 39/16* (2006.01)

(52) U.S. Cl.
  CPC ............... *A61L 2/087* (2013.01); *A61L 2/10* (2013.01); *A61M 1/025* (2013.01); *A61M 1/0209* (2013.01); *A61M 39/105* (2013.01); *A61M 39/1055* (2013.01); *A61M 39/26* (2013.01); *B08B 7/0057* (2013.01); *B08B 9/021* (2013.01); *B08B 9/027* (2013.01); *A61M 2039/1033* (2013.01); *A61M 2039/1038* (2013.01); *A61M 2039/167* (2013.01); *A61M 2039/261* (2013.01); *A61M 2039/263* (2013.01); *A61M 2039/268* (2013.01); *B08B 2209/027* (2013.01); *B08B 2230/01* (2013.01)

(58) Field of Classification Search
  CPC ....... B08B 7/0057; B08B 9/021; B08B 9/027; B08B 2209/027; B08B 2230/01; A61L 2/10; A61L 2/087; A61L 2/081; A61L 2/04; A61L 2/07
  See application file for complete search history.

(56) References Cited

U.S. PATENT DOCUMENTS 10,351,271 B2 * 7/2019 Py ..................... B65B 39/004
2013/0292592 A1 11/2013 Py

FOREIGN PATENT DOCUMENTS

WO       2012125457 A1   9/2012
WO   WO-2013153722 A1 * 10/2013 ........ A61M 39/1011

OTHER PUBLICATIONS

European Patent Office, extended European Search Report, counterpart EP Appl. No. 18214466.7, 9 pages, (dated Jul. 3, 2019).

* cited by examiner

FIG. 8

SYSTEM AND METHOD OF STERILELY CONNECTING FLUID PATHWAYS

CROSS-REFERENCE TO RELATED APPLICATIONS

This application claims the benefit of U.S. Provisional Patent App. No. 62/608,995 filed Dec. 21, 2017, which is expressly incorporated herein by reference in its entirety.

FIELD OF THE DISCLOSURE

The present disclosure relates generally to systems and methods of sterilely connecting fluid pathways and, in particular to systems and methods for sterilely connecting fluid pathways with a reusable connector within a biological fluid circuit without excising fluid pathway material.

BACKGROUND

Processing or collection of biological fluid such as blood components, biological fluids, or medical fluids may involve using a reusable hardware and a disposable fluid circuit adapted for mounting or other association with the reusable hardware. The fluid circuit may include containers such as plastic containers, vials, and associated tubing that define flow paths through the circuit.

A disposable fluid circuit may include plastic containers and tubes that are pre-connected and pre-assembled to maintain sterility. In some processing systems and methods, containers including liquids such as anticoagulant, saline, wash solution, storage media, treating agents, biological fluids, etc., may likewise be pre-attached to the disposable fluid circuit, thereby creating a "closed" system. A "closed" system is one where the interior of the system, i.e., internal flow paths, separation chambers, etc., are not exposed or "opened" to the outside environment.

SUMMARY

According to an exemplary embodiment, the present disclosure is directed to a tube connector for a fluid circuit system comprising a housing. A first opening is configured to receive a first length of tubing in communication with a first chamber. A second opening is configured for communicating with the first chamber when the tube connector is in an open configuration but not in a closed configuration. A third opening is configured to receive a second length of tubing in communication with a second chamber. A fourth opening is configured for communicating with the second chamber when the tube connector is in the open configuration but not in the closed configuration. The second opening and the fourth opening are configured to engage each other to form a third chamber.

According to an exemplary embodiment, the present disclosure is directed to a method of sterilely connecting two fluid pathways. Provided is a first connector comprising a first chamber and a first open end and configured to connect to a first fluid pathway. The first chamber is configured to communicate with the first fluid pathway and the first open end when the first connector is in an open configuration but not in a closed configuration. Provided is a second connector comprising a second chamber and a second open end and configured to connect to a second fluid pathway. The second chamber is configured to communicate with the second fluid pathway and the second open end when the second connector is in an open configuration but not in a closed configuration. The first open end and the second open end are configured for engagement to form a third chamber. The third chamber is configured to communicate with the first chamber when the first connector is in the open configuration but not in the closed configuration and communicate with the second chamber when the second connector is in the open configuration but not in the closed configuration. The first open end and the second open end forming the third chamber comprises a first material at least partially permeable to a sterilization energy source for sterilizing contents of the third chamber. A first portion of the first connector surrounding the first chamber and a second portion of the second connector surrounding the second chamber comprise a second material less permeable to the sterilization energy source. Applying the sterilization energy source to the third chamber upon engagement of the first and second open ends when the first and second connectors are in the closed configuration and subsequently opening the first and second connectors to the open configuration allows sterile fluid from the first chamber to cross the third chamber into the second chamber while maintaining sterility.

According to an exemplary embodiment, the present disclosure is directed to a sterile tube connector for a fluid circuit system comprising a housing. A first opening is configured to receive a first length of tubing in communication with a first chamber. A second opening is configured for communicating with the first chamber when the tube connector is in an open configuration but not in a closed configuration. The second opening is configured to reversibly engage a third opening to form a second chamber. The third opening is configured for communicating with a second length of tubing. A first portion of the housing forming the first opening comprises a material at least partially permeable to a sterilization energy source for sterilizing contents of the second chamber.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In the course of biological fluid processing, a variety of fill/finish operations, and/or any fluid processing requiring sterile connection of fluid paths, one common method for sterilely connecting fluid paths is by use of a sterile weld device, which takes two tubing segments of compatible sizes and materials and performs a welding operation in which the segments of tubing are clamped, cut, aligned with each other, and melted to fuse the two segments together. An operator may manually load tubing segments into the sterile weld device serially for each welding operation. Using a sterile weld device may require additional disposable components, e.g., blades, cartridges, and may include some portion of a tubing segment being excised, thereby shortening the tubing segment with each sterile weld operation. In instances in which fluidic circuits are frequently and routinely attached to multiple other circuits, e.g., fill/finish operations in which a bulk fluid within a circuit is aliquoted into several, separate containers/fluidic circuits, sterile welding may call for each circuit to have long lengths of tubing to accommodate tubing length consumption with each welding event.

Some embodiments may decrease reliance on manual interventions common even in automated processes of multiple welding operations involving complex loading and unloading procedures.

Some embodiments may minimize or obviate tracking tubing lengths being consumed for multiply-welded tubing segments.

Some embodiments may enable fluid circuit connections even when the segments to be connected are not made of compatible materials or employ dissimilar sizes or are otherwise not easily implemented with welding systems."

It may be desirable to durably create and maintain sterile fluid pathways between two closed fluidic circuits without compromising sterility, without taking on aseptic risk, and without consuming tubing segments with each connection event.

Some embodiments may obviate the use of additional disposable components in sterilely connecting fluid pathways together.

Some embodiments may allow for repeated sterile connections between two fluid pathway segments without shortening segment lengths each time the connection is performed.

Some embodiments may allow fluid circuits to have shorter lengths of tubing without accommodating tubing length consumption with each welding event.

Some embodiments may decrease variability in the pathway joining process and be conducive to automation.

Systems and methods for sterile processing of fluid are disclosed herein. The systems disclosed may include a fluid processing apparatus and one or more disposable processing circuits adapted for association with the processing apparatus. The processing apparatus may be any apparatus for processing of fluids in sterile environments. Examples include apparatuses for cell processing, apheresis, infusion, transfusion, fractionation, cell washing, dialysis, molecular and medical diagnostics, forensics, anesthesia, etc.

While primarily described herein with reference to a fluid processing system used in a blood separation machine, the described concepts may be applied to any other type of fluid circuit system and/or fill/finish operations in which sterile connection is desired. The processing apparatus may be capable of effecting the separation of a biological fluid that includes biological cells into two or more components or fractions. Thus, the processing apparatus may generate conditions which allow for the separation of a biological fluid into selected components or fractions. In one embodiment, an apparatus that uses a spinning porous membrane to separate one component from other components may be used for separating biological fluid into its constituent components or fractions. An example of a spinning membrane may be found in U.S. Pat. No. 5,194,145 to Schoendorfer and International Application No. PCT/US2012/028492, filed Mar. 9, 2012, both of which are incorporated herein in their entireties, although any suitable membrane separator may be used. In another embodiment, an apparatus that uses centrifugal separation principles to separate one component from other components may be used for separating biological fluid into its constituent components or fractions. An exemplary centrifugal separator is disclosed in U.S. Pat. No. 5,868,696, which is incorporated by reference in its entirety, although any suitable centrifugal separator may be used. In other embodiments, the described concepts may be applied to blood pack units, transfer packs, or other static fluid systems.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path.

Figure 1:
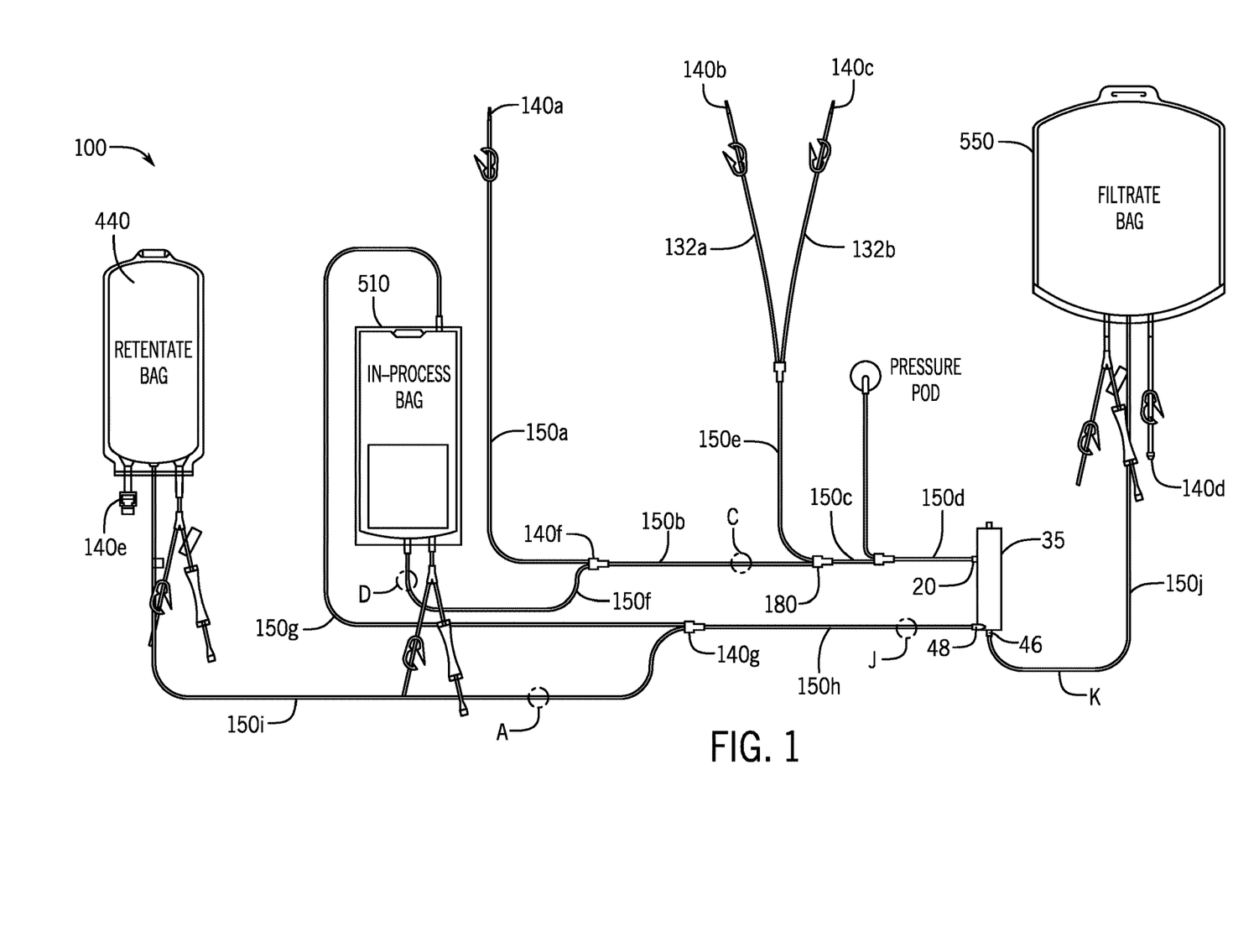
FIG. 1 is a schematic view of a disposable fluid circuit that may be used in combination with a reusable processing apparatus, according to an exemplary embodiment.
Figure 2:
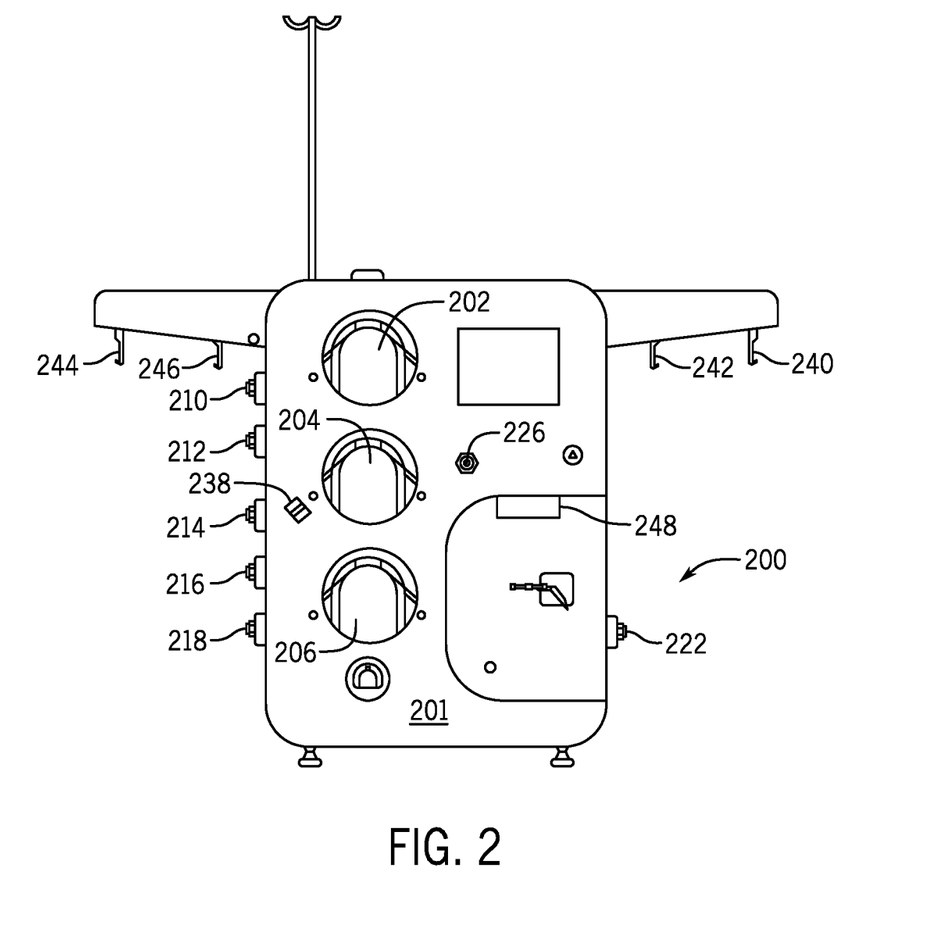
FIG. 2 is an enlarged view of a front panel of a reusable processing apparatus, according to an exemplary embodiment.

Referring now to FIG. 1, a fluid circuit 100 is shown, according to an exemplary embodiment. In various embodiments, fluid circuit 100 may be configured to associate with a cell processing machine 200 (FIG. 2) that separates source blood into blood components. For example, a cell processing device 200 may include a membrane separator 35 or other blood separation device that processes whole blood or other suspensions of biological material into its constituent components (e.g., red blood cells, plasma, platelets, etc.). The cell processing device may associate with fluid circuit 100 which may be configured to convey fluid to and from the separator or other separation device to/from/between multiple collection containers 440, 510, 550. Such fluids may be routed in fluid circuit 100 via lengths of fluid pathways or tubing 150a-j. In an embodiment in which biological fluids such as blood are handled, tubing 150a-j may be formed of non-reactive materials and may be configured for a single use (e.g., intended to be disposed after each use). In some embodiments, tubing 150a-j may also be formed of a relatively flexible material, such as PVC or silicone. In one exemplary embodiment, tubing 150*a-j* may comprise an outer diameter of less than 3 cm with a hardness of approximately 70 shore A.

Tubing 150*a-j* may be coupled to the various components of fluid circuit 100 and/or to other lengths of tubing 150*a-j* via connectors 140*a-g*. For example, tubing 150*a* and its corresponding connector 140*a* may be connected to a container 440 via connector 140*e*. In various embodiments, connectors 20 may be inline connectors coupling two lengths of tubing 150*a-j* together, Y-connectors or T-connectors coupling more than two lengths of tubing 150*a-j* together, connectors configured to couple a length of tubing 150*a-j* to the cell processing device 200, connectors configured to couple a length of tubing 150*a-j* to a collection container 440, 510, 550, or a connector for coupling a length of tubing 150*a-j* to any number of lengths of tubing 150*a-j*. A length of tubing 150*a-j* and a corresponding connector 140*a-g* may be bonded together to form a hermetic seal, thereby preventing or minimizing the escape of fluid from fluid circuit 100 where the length of tubing 150*a-j* and the connector 140*a-g* are joined. After the collection of the fluids is complete, a collection container 440, 510, 550 may be separated from fluid circuit 100 by disconnecting connector 140*a-g* from a counterpart connector 140*a-g* of the fluid circuit 100.

Figure 3:
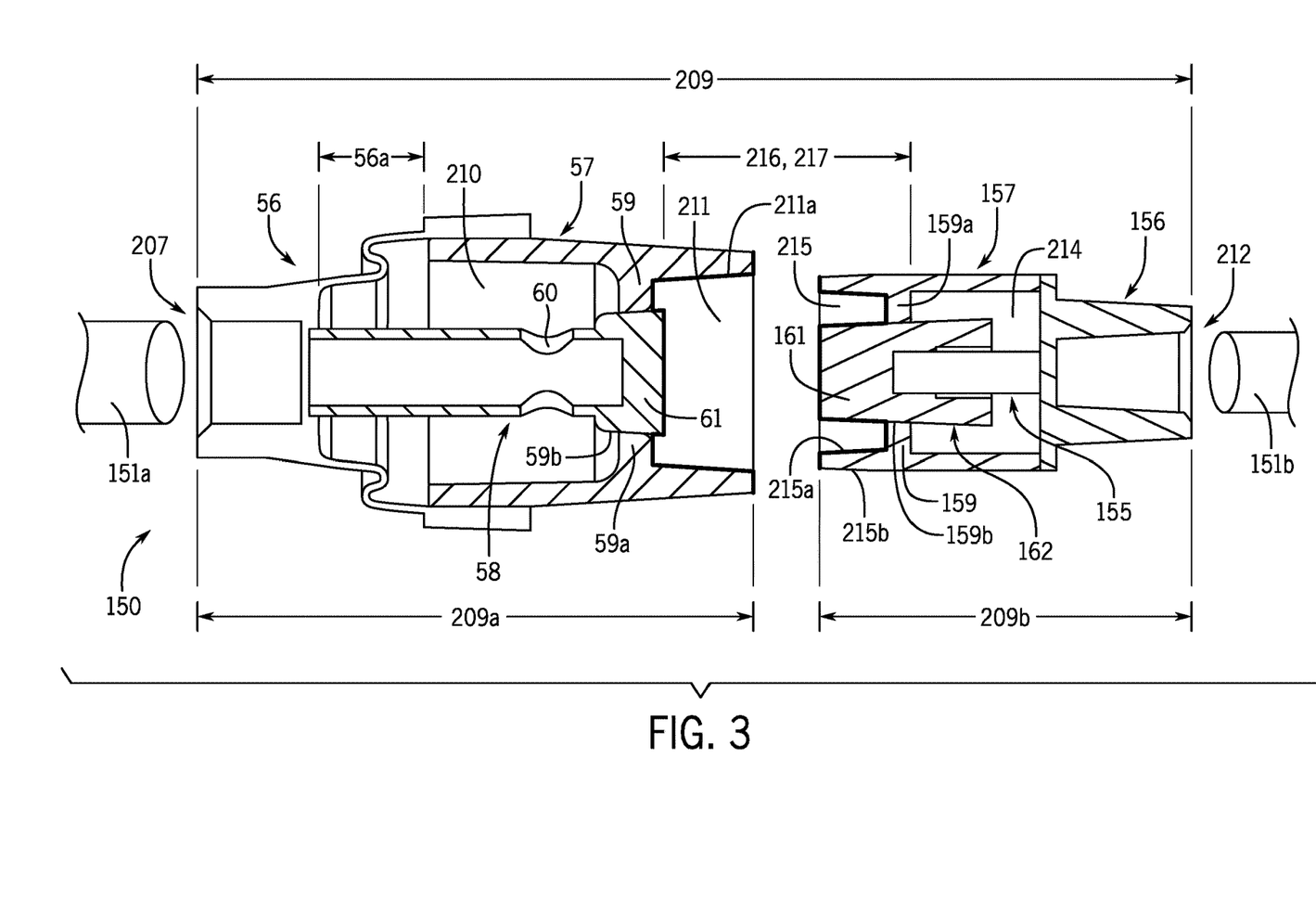
FIG. 3 is a longitudinal cross section view of sub-housings of a connector, according to an exemplary embodiment.

Referring now to FIG. 3, a longitudinal cross section view of a connector 150 is shown, according to an exemplary embodiment. Connector 150 may be used in a fluid circuit, such as fluid circuit system 100 shown in FIG. 1 or in another such fluid circuit. Connector 150 may generally be configured to receive and retain inserted lengths of tubing 151*a*, 151*b* or otherwise form a hermetic seal to prevent fluid from leaving the fluid circuit. In one embodiment, tubing 151*a*, 151*b* may be coupled to the connector 150 with a solvent adhesive. In other embodiments, tubing 151*a*, 151*b* may be coupled to connector 150 by another suitable method, such as a welded connection or a mechanical connection (e.g., clamped or compressed between two portions of connector 150), or connector 150 may be over- or under-molded around tubing 151*a*, 151*b*. In one embodiment, a portion of the connector 150 may be constructed using a relatively stiff material, such as a medium durometer (e.g., 40-80A durometer) PVC material, in comparison to that of tubing 151*a*, 151*b*.

The connector 150 may comprise a generally hollow and cylindrical housing 209. In one embodiment, the housing 209 may comprise a sub-housing 209*a* corresponding to one fluid pathway 151*a* and another sub-housing 209*b* corresponding to another fluid pathway 151*b*. Sub-housings 209*a* and 209*b* may be configured to reversibly or irreversibly engage each other in sealing engagement. Each sub-housing 209*a* and 209*b* may also function as a connector per se, configured for engagement with any other connector having a complementary shape.

Sub-housing 209*a* may comprise a socket segment 56 connected to a connector segment 57. The socket segment 56 may comprise an opening 207 configured to receive a fluid pathway 151*a*, e.g. a length of tubing. The opening 207 may have any generally hollow shape (e.g., circular, square, ovoid, etc.), depending on the shape of the cross-section of the fluid pathway to be inserted. The opening 207 may be in communication with a chamber 210 formed by the socket segment 56 and the connector segment 57. The connector segment 57 may comprise a valve 59 controlling fluid flow between the chamber 210 and an opening 211 of the connector segment 57. The valve 59 may comprise a wall 59*a* separating the chamber 210 and the opening 211 that is generally perpendicular to the length of the tubing 151*a* and includes an aperture 59*b*. Communication between the opening 207 of the socket portion 56 and the chamber 210 may be effected by a hollow channel 58 (e.g., plunger) that extends from the opening 207 of the socket portion 56 through the chamber 210 into the aperture 59*b* and is blocked at a tapered end 61. The channel 58 may comprise at least one orifice 60 disposed within the chamber 210 that allows fluid communication between the opening 207 and the chamber 210. The tapered end 61 of the plunger 58 may be disposed through the aperture 59*b* such that the tapered end 61 and the aperture 59*b* form a hermetic seal when the first sub-housing is in a closed configuration. The diameter of the tapered end 61 disposed on the chamber side of the aperture 59*b* may be smaller than the diameter of the aperture 59*b*, while the diameter of the tapered end 61 disposed on the side of the aperture of the opening 211 may be larger than the diameter of the aperture 59*b*. The tapering of the end 61 of the plunger 58 may ensure that the end 61 does not retract back through the aperture 59*b* towards the chamber 210.

An open configuration of the first sub-housing 209*a* may be effected by compression of the sub-housing 209*a* relative to the plunger/channel 58. In one embodiment, the plunger 58 may be attached to a tension spring (not illustrated) of the socket portion 56 such that in the resting state of the sub-housing 209, tension within the plunger 58 maintains a closed configuration, driven by a spring force pulling the plunger 58 towards the opening 207 and opposed by the valve 59 holding the tapered end 61 in place. FIG. 3 shows the socket portion 56 having a compliant segment 56*a*. The compliant segment 56*a* may be manually compressible from the resting state. Although FIG. 3 shows the socket portion 56 including the compliant segment 56*a*, a compliant segment may be incorporated into either or both of the portions 56 and 57. Compression of the compliant segment 56*a* may induce translational motion of the valve 59 towards the opening 207 relative to the tapered end 61 of the plunger 58. Translational motion induced by compression may open the seal between the tapered end 61 and the aperture 59*b* due to the difference in diameters between the end 61 and the aperture 59*b* to allow fluid flow between the chamber 210 and the opening 211.

Sub-housing 209*b* may comprise a socket segment 156 connected to a connector segment 157. The socket segment 156 may comprise an opening 212 configured to receive a fluid pathway 151*b*, e.g. a length of tubing. The opening 212 may be in communication with a chamber 214 formed by the socket segment 156 and the connector segment 157. The connector segment 157 may comprise a valve 159 controlling fluid flow between the chamber 214 and an opening 215 of the connector segment 157. The valve 159 may comprise a wall 159*a* separating the chamber 214 and the opening 215 that is generally perpendicular to the length of the tubing 151*b* and includes an aperture 159*b*. A compressible member 158 attached to a stopper 162 having a tapered end 161 may extend from the socket portion 156 through the chamber 214 into the aperture 159*b* until the tapered end 161 seals the aperture 159*b*. The tapered end 161 of the stopper 162 may be disposed through the aperture 159*b* such that the tapered end 161 and the aperture 159*b* form a hermetic seal when the sub-housing 209*b* is in a closed configuration. The diameter of the tapered end 161 disposed on the chamber side of the aperture 159*b* may be larger than the diameter of the aperture 159*b*, while the diameter of the tapered end 161 disposed on the side of the opening 215 may be smaller than the diameter of the aperture 159b.

An open configuration of the sub-housing 209b may be effected by compression of the compressible member 158 relative to the sub-housing 209b. In one embodiment, the compressible member 158 may be attached to a compression spring (not illustrated) of the socket portion 156 such that in the resting state of the sub-housing 209b, compression within the compressible member 158 maintains a closed configuration, driven by a spring force pushing the stopper 162 towards the opening 215 and opposed by the valve 159 holding the tapered end 161 in place. FIG. 3 shows the socket portion 56 having a compliant segment 56a. Compression of the compressible member 158 may induce translational motion of the compressible member 158 and stopper 162 towards the opening 212 relative to the valve 159. Translational motion induced by compression may open the seal between the tapered end 161 and the aperture 159b due to the difference in diameters between the end 161 and the aperture 159b to allow fluid flow between the chamber 214 and the opening 215.

Figure 4:
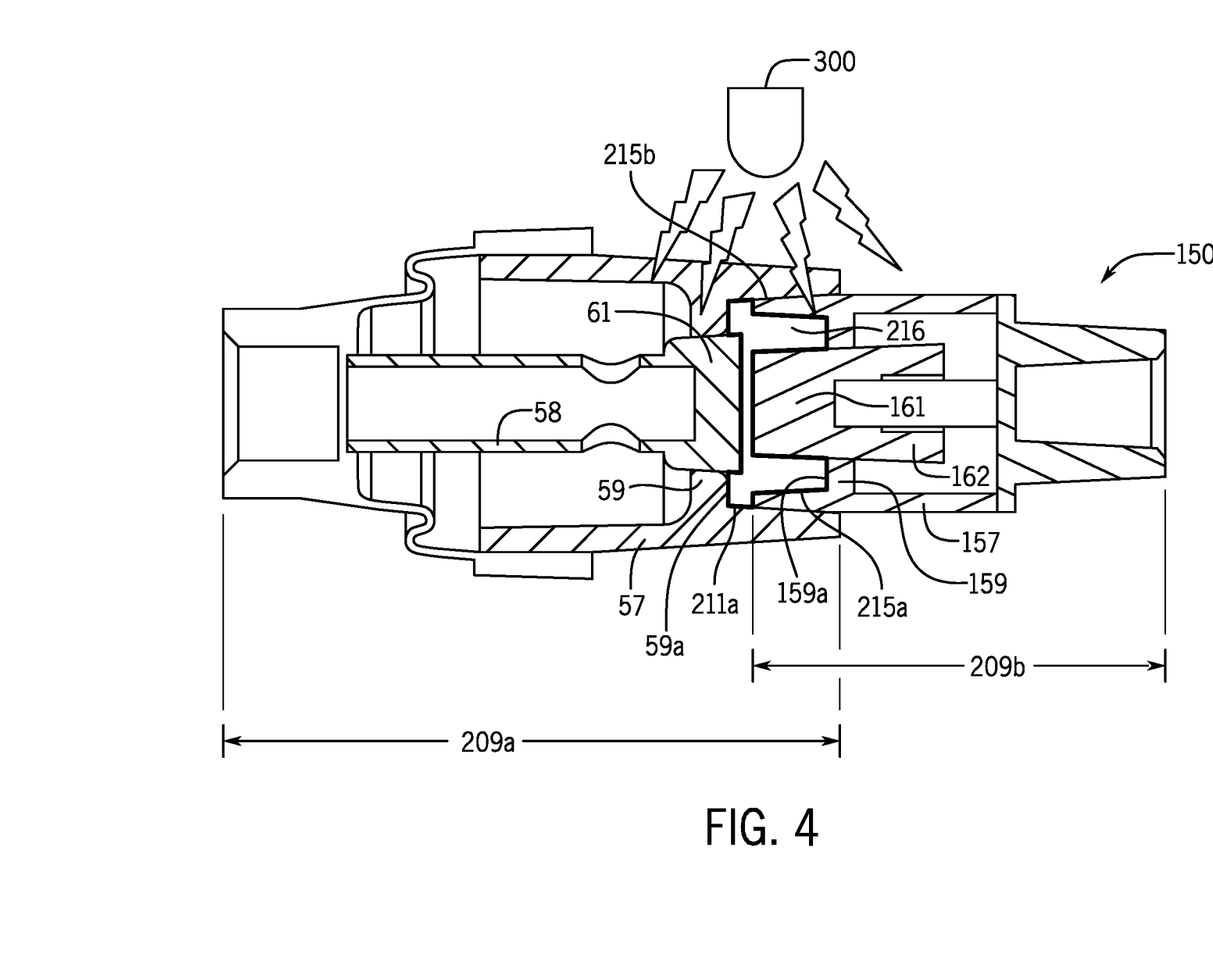
FIG. 4 is a longitudinal cross section view of the connector of FIG. 4 in which the sub-housings are in engagement, according to an exemplary embodiment.

Referring now to FIG. 4, a longitudinal cross section view of the connector 150 is shown in which sub-housings 209a and 209b are engaged with each other in sealing engagement, according to an exemplary embodiment. FIG. 4 depicts both sub-housings 209a and 209b in closed configurations. The opening 211 of the connector segment 57 of the sub-housing 209a and the opening 215 of the connector segment 157 of the sub-housing 209b may be configured to form an enclosed chamber 216. The inner surface 211a of the connector portion 57 forming the opening 211, the wall 59a of valve 59, the tapered end 61 of plunger 58, the inner surface 215a of the connector portion 157 forming the opening 215, the wall 159a of valve 159, and/or the tapered end 161 of stopper 162 may together form the walls of the enclosed chamber 216. The connector segments 57 and 157 may be configured such that the outer surface of one segment forms a friction fit, interference fit, Luer fit, threaded fit, etc., with the other segment. For example, the outer surfaces 215b of the connector segment 157 may be configured to hermetically engage with the inner surfaces 211a of the connector segment 57.

Once the chamber 216 is hermetically sealed, surfaces 59a, 61, 159a, 161, 211a, 215a previously open to the atmosphere may be sterilized. A sterilization energy source 300 configured with a known germicidal dose may be applied to the newly formed chamber 216. In one embodiment, the sterilization energy source may comprise a UVC emitter (e.g., LED, CFL bulb). In another embodiment, the sterilization energy source may comprise heat, steam, ebeam, gamma rays, etc.

It may be desirable to selectively apply sterilization energy to the chamber 216 while minimizing exposure of the germicidal dose of energy to other portions of the connector 150. For example, the socket portion 56 of sub-housing 209a and the socket segment 156 of sub-housing 209b and any fluid contained therein may not require sterilization and may comprise biological materials sensitive to the sterilization energy. Therefore, it may be desirable for the socket portions 56 and 156 to comprise a material with low permeability to the sterilization energy and for the connector portions 57 and 157 to comprise a material with high permeability to the sterilization energy. In an embodiment in which the sterilization energy source comprises UVC, the connector portions 57 and 157 may comprise a substantially UVC-transparent material, such as cyclic olefin copolymer (COC), poly(methyl methacrylate) (PMMA), polymethylpentene (PMP or TPX), and/or quartz glass, and the socket portions 56 and 156 may comprise a substantially UVC-opaque material, such as polycarbonate, PVC, and/or ABS (acrylonitrile butadiene styrene). Opaqueness may be accomplished or enhanced by colorants and/or pigments. In an embodiment in which the sterilization energy source comprises heat, steam, ebeam, gamma rays, etc., connector portions 56, 57, 156, and 157 may be comprised of heat compatible material, such as polycarbonate, PVC, and/or ABS, and the socket portions 56 and 156 may further comprise a substantially heat transmissive material and may even comprise heat resistive material, such as polyurethane and/or silica aerogel. Referring to FIG. 3, in one embodiment, connector portions 57 and 157 may be made of one material permeable to the sterilization energy for a segment 217 surrounding the sterilization chamber 216 and another material less permeable to the sterilization energy for the remaining portions of connector portions 57 and 157.

Figure 5:
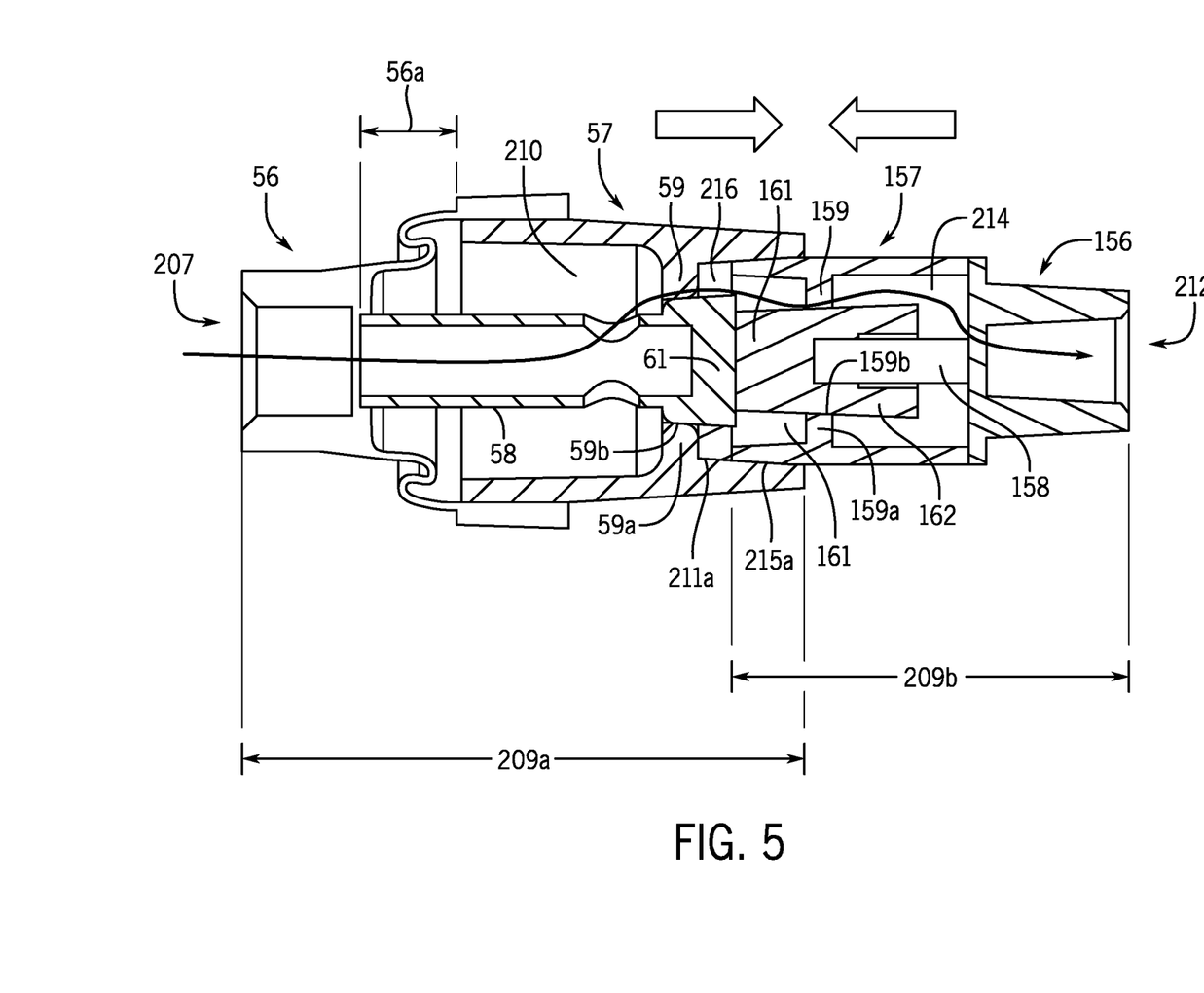
FIG. 5 is a longitudinal cross section view of the connector of FIGS. 3-4 in which fluid communication is open between the sub-housings, according to an exemplary embodiment.

Referring to FIG. 5, once the chamber 216 and corresponding surfaces 59a, 61, 159a, 161, 211a, 215a have been sterilized, fluid communication may be opened between chambers 210 and 216. Sub-housing 209a may be shifted to an open configuration by breaking the seal between the tapered end 61 of the plunger 58 and the aperture 59b by compressing the sub-housing 209a relative to the plunger/channel 58, which in one embodiment may be implemented by compressing the compliant segment 56a of the socket portion 56. Translational motion of the valve 59 may be induced towards the opening 207 relative to the tapered end 61 of the plunger 58 and thereby open fluid flow from the chamber 210 to the chamber 216. Fluid from the sub-housing 209a may flow from within the channel 58 through the orifice 60 into the chamber 210 through the valve aperture 59b and into the sterilization chamber 216.

Sub-housing 209b may be shifted to an open configuration by breaking the seal between the tapered end 161 of the stopper 162 and the aperture 159b. Once sub-housing 209a is shifted to an open configuration and the translational motion of the valve 59 is induced towards the opening 207 relative to the tapered end 61 of the plunger 58, the engagement (friction fit, interference fit, Luer fit, threaded fit, etc.) between the connector segment 157 and the connector segment 57 may pull sub-housing 209b towards the compliant segment 56 while the tapered end 61 of the plunger 58 exerts an opposite force against the stopper 162. The opposite force against the stopper 162 may induce compression of the compressible member 158 of the socket segment 156, leading to translational motion of the compressible member 158 and stopper 162 towards the opening 212 relative to the valve 159, opening the seal between the tapered end 161 and the aperture 159b. Fluid from the sterilization chamber 216 may flow through the valve aperture 159b into the chamber 214 and into the opening 212 of sub-housing 209b.

When fluid communication is no longer desired and/or different fluid connections are desired, the sub-housings 209a and 209b may be disconnected by relieving compression of compliant segment 56a and compressible member 158 to shift both connectors to the closed configuration. The engagement between the connector segment 157 and the connector segment 57 forming the sterilization chamber 216 may be severed, and the connectors 209a and 209b may be re-used with other connections.

Figure 6A:
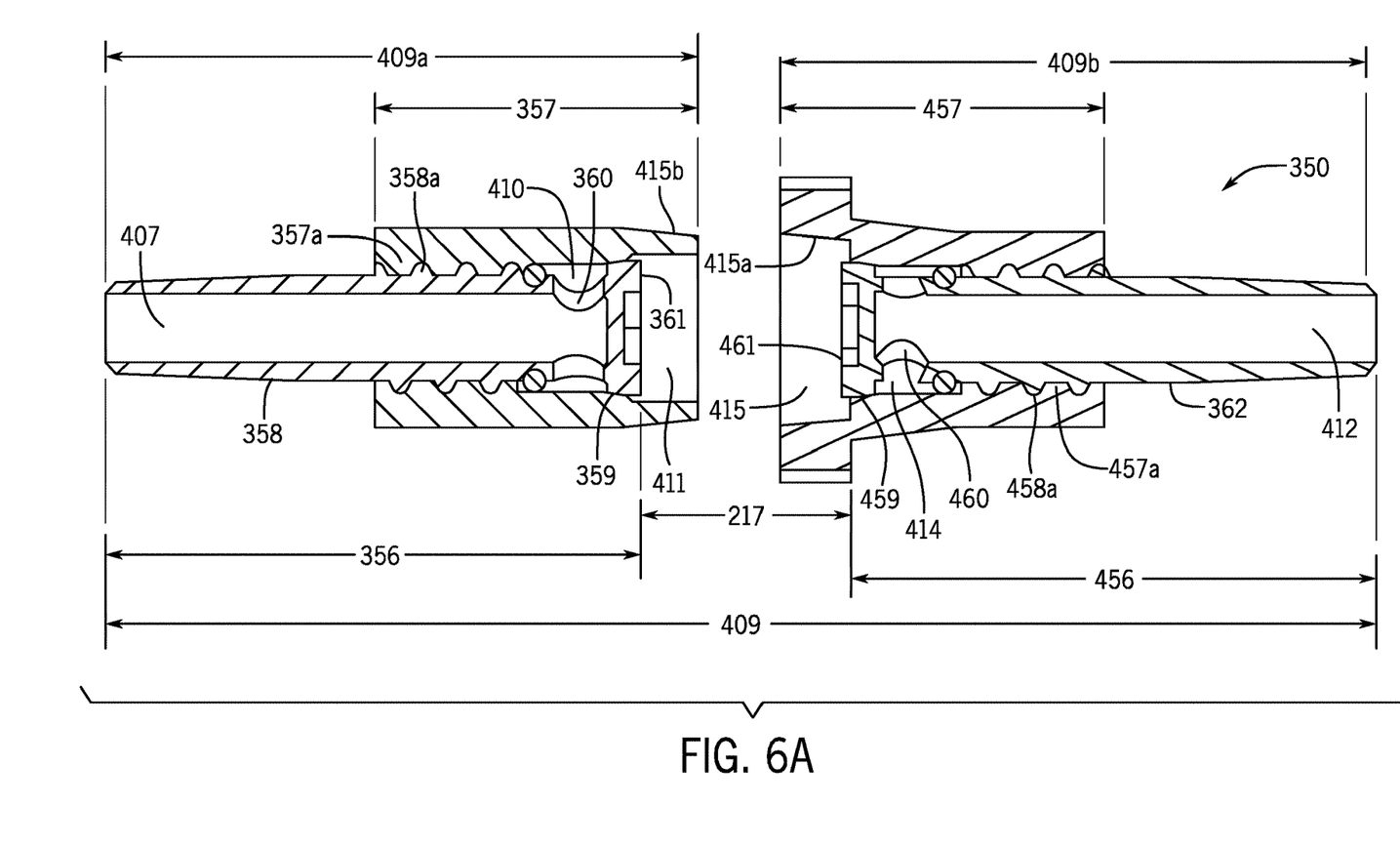
FIG. 6A is a longitudinal cross section view of sub-housings of a connector, according to another exemplary embodiment.

Referring now to FIG. 6A, a longitudinal cross section view of another embodiment of a connector 350 is shown. Connector 350 may generally be configured to receive and retain lengths of tubing or otherwise form a hermetic seal to prevent fluid from leaving as sterile system. The connector 350 may comprise a generally hollow and cylindrical housing 409. In one embodiment, the housing 409 may comprise a sub-housing 409a corresponding to one fluid pathway another sub-housing 409b corresponding to another fluid pathway. Sub-housings 409a and 409b may be configured to reversibly or irreversibly engage each other in sealing engagement. Each sub-housing 409a and 409b may also function as a connector per se, configured for engagement with any other connector having a complementary shape.

Sub-housing 409a may comprise a socket segment 356 connected to a connector segment 357. The socket segment 356 may comprise an opening 407 configured to receive a fluid pathway, e.g. a length of tubing. The opening 207 may be in communication with a chamber 410 formed by the socket segment 356 and the connector segment 357. The connector segment 357 may comprise a small diameter portion 359 disposed between the chamber 410 and an opening 411 of the connector segment 357. Communication between the opening 407 of the socket portion 356 and the chamber 410 may be effected by a hollow channel 358 that extends from the opening 407 of the socket portion 356 through the chamber 410 past the small diameter portion 359 and is blocked at an end 361. The channel 358 may comprise at least one orifice 360 disposed within the chamber 410 that allows fluid communication between the opening 407 and the chamber 410. The end 361 of the channel 358 may cover the small diameter portion 359 such that the end 361 and the small diameter portion 359 form a hermetic seal separating the chamber 410 and the opening 411 when the first sub-housing is in a closed configuration. The diameter of the end 361 disposed on the chamber side of the small diameter portion 359 may be smaller than the diameter of the small diameter portion 359, while the diameter of the end 361 disposed on the side of the opening 411 may be larger than the diameter of the small diameter portion 359. The differences in diameters of the end 361 of the channel 358 may ensure that the end 361 does not retract back into the chamber 410.

An open configuration of the first sub-housing 409a may be effected by rotation of the socket segment 356 and connector segment 357 relative to each other. In one embodiment, the channel 358 may have outer threads 358a configured to mate with corresponding inner threads 357a of the connector portion 357 such that in the closed configuration of the sub-housing 409a, outer and inner threads 358a and 357a are tightly fastened, with the end 361 tightly sealed against the small diameter portion 359. Rotation of the socket segment 356 and connector segment 357 relative to each other may induce translational motion of the channel 358 and end 361 towards the opening 411 relative to the small diameter portion 359 of the connector portion 357. The translational motion may open the seal between the end 361 and the small diameter portion 359 due to the difference in diameters between the end 361 and the small diameter portion 359 to allow fluid flow between the chamber 410 and the opening 411.

Sub-housing 409b may comprise a socket segment 456 connected to a connector segment 457. The socket segment 456 may comprise an opening 412 configured to receive a fluid pathway, e.g., a length of tubing. The opening 412 may be in communication with a chamber 414 formed by the socket segment 456 and the connector segment 457. The connector segment 457 may comprise a small diameter portion 459 disposed between the chamber 414 and an opening 415 of the connector segment 457. Communication between the opening 412 of the socket portion 456 and the chamber 414 may be effected by a hollow channel 362 that extends from the opening 412 of the socket portion 456 through the chamber 414 past the small diameter portion 459 and is blocked at an end 461. The channel 362 may comprise at least one orifice 460 disposed within the chamber 414 that allows fluid communication between the opening 412 and the chamber 414. The end 461 of the channel 362 may cover the small diameter portion 459 such that the end 461 and the small diameter portion 459 form a hermetic seal separating the chamber 414 and the opening 415 when the first sub-housing is in a closed configuration. The diameter of the end 461 disposed on the chamber side of the small diameter portion 459 may be smaller than the diameter of the small diameter portion 459, while the diameter of the end 461 disposed on the side of the opening 415 may be larger than the diameter of the small diameter portion 459. The differences in diameters of the end 461 of the channel 362 may ensure that the end 461 does not retract back into the chamber 414.

An open configuration of the second sub-housing 409b may be effected by rotation of the socket segment 456 and connector segment 457 relative to each other. In one embodiment, the channel 362 may have outer threads 458a configured to mate with corresponding inner threads 457a of the connector portion 457 such that in the closed configuration of the sub-housing 409b, outer and inner threads 458a and 457a are tightly fastened, with the end 461 tightly sealed against the small diameter portion 459. Rotation of the socket segment 456 and connector segment 457 relative to each other may induce translational motion of the channel 362 and end 461 towards the opening 415 relative to the small diameter portion 459 of the connector portion 457. The translational motion may open the seal between the end 461 and the small diameter portion 459 due to the difference in diameters between the end 461 and the small diameter portion 459 to allow fluid flow between the chamber 414 and the opening 415.

Figure 6B:
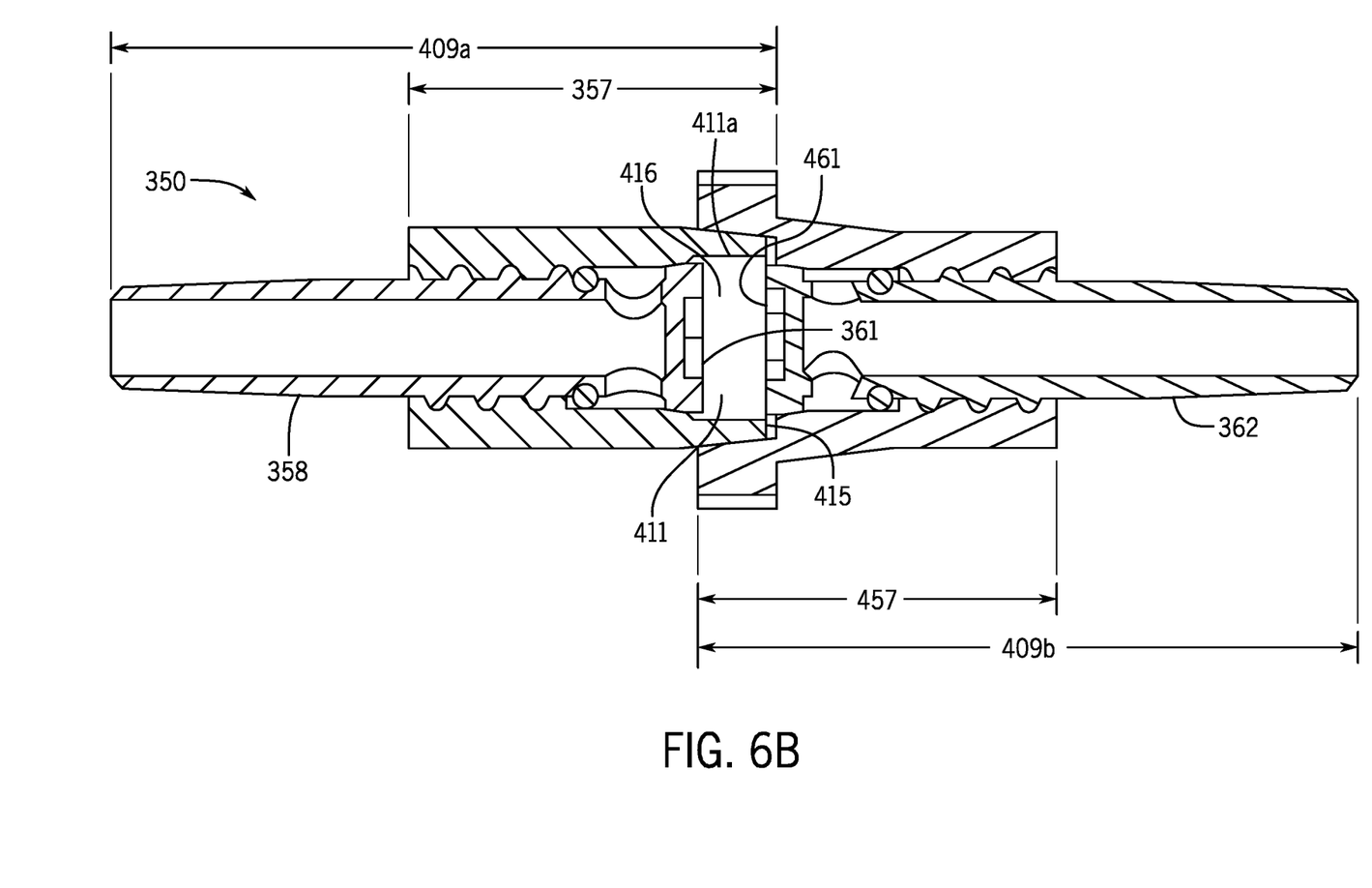
FIG. 6B is a longitudinal cross section view of the connector of FIG. 6A in which the sub-housings are in engagement, according to an exemplary embodiment.

Referring now to FIG. 6B, a longitudinal cross section view of the connector 350 is shown in which sub-housings 409a and 409b are engaged with each other in sealing engagement, according to an exemplary embodiment. FIG. 6B depicts both sub-housings 409a and 409b in closed configurations. The opening 411 of the connector segment 357 of the sub-housing 409a and the opening 415 of the connector segment 457 of the sub-housing 409b may be configured to form an enclosed chamber 416. The inner surface 411a of the connector portion 357 forming the opening 411, the end 361 of the channel 358, and/or the end 461 of the channel 362 may together form the walls of the enclosed chamber 416. The connector segments 357 and 457 may be configured such that the outer surface of one segment forms a friction fit, interference fit, Luer fit, threaded fit, etc., with the other segment. For example, the outer surfaces 415b (FIG. 6A) of the connector segment 357 may be configured to hermetically engage with the inner surfaces 415a of the connector segment 457. Once the chamber 416 is hermetically sealed, surfaces 411a, 361, 461 previously open to the atmosphere may be sterilized as described previously in reference to FIG. 4.

It may be desirable to selectively apply sterilization energy to the chamber 416 while minimizing exposure of the germicidal dose of energy to other portions of the connector 350. For example, the socket portion 356 of sub-housing 409a and the socket segment 456 of sub-housing 409b and any fluid contained therein may not require sterilization and may comprise biological materials sensitive to the sterilization energy. Therefore, it may be desirable for the socket portions 356 and 456 to comprise a material with low permeability to the sterilization energy and for the connector portions 357 and 457 to comprise a material with high permeability to the sterilization energy. In an embodiment in which the sterilization energy source comprises UVC, the connector portions 357 and 457 may comprise a substantially UVC-transparent material, such as cyclic olefin copolymer (COC), poly(methyl methacrylate) (PMMA), polymethylpentene (PMP or TPX), and/or quartz glass, and the socket portions 356 and 456 may comprise a substantially UVC-opaque material, such as polycarbonate, PVC, and/or ABS. In an embodiment in which the sterilization energy source comprises heat, steam, ebeam, gamma rays, etc., the connector portions 357 and 457 may comprise a heat conductive material, such as polycarbonate, PVC, and/or ABS, and the socket portions 356 and 456 may further comprise a substantially heat transmissive material and may even comprise heat resistive material, such as polyurethane and/or silica aerogel. Referring to FIG. 6A, in one embodiment, connector portions 357 and 457 may be made of one material permeable to the sterilization energy for a segment 217 surrounding the sterilization chamber 416 and another material less permeable to the sterilization energy for the remaining portions of connector portions 357 and 457.

Figure 7:
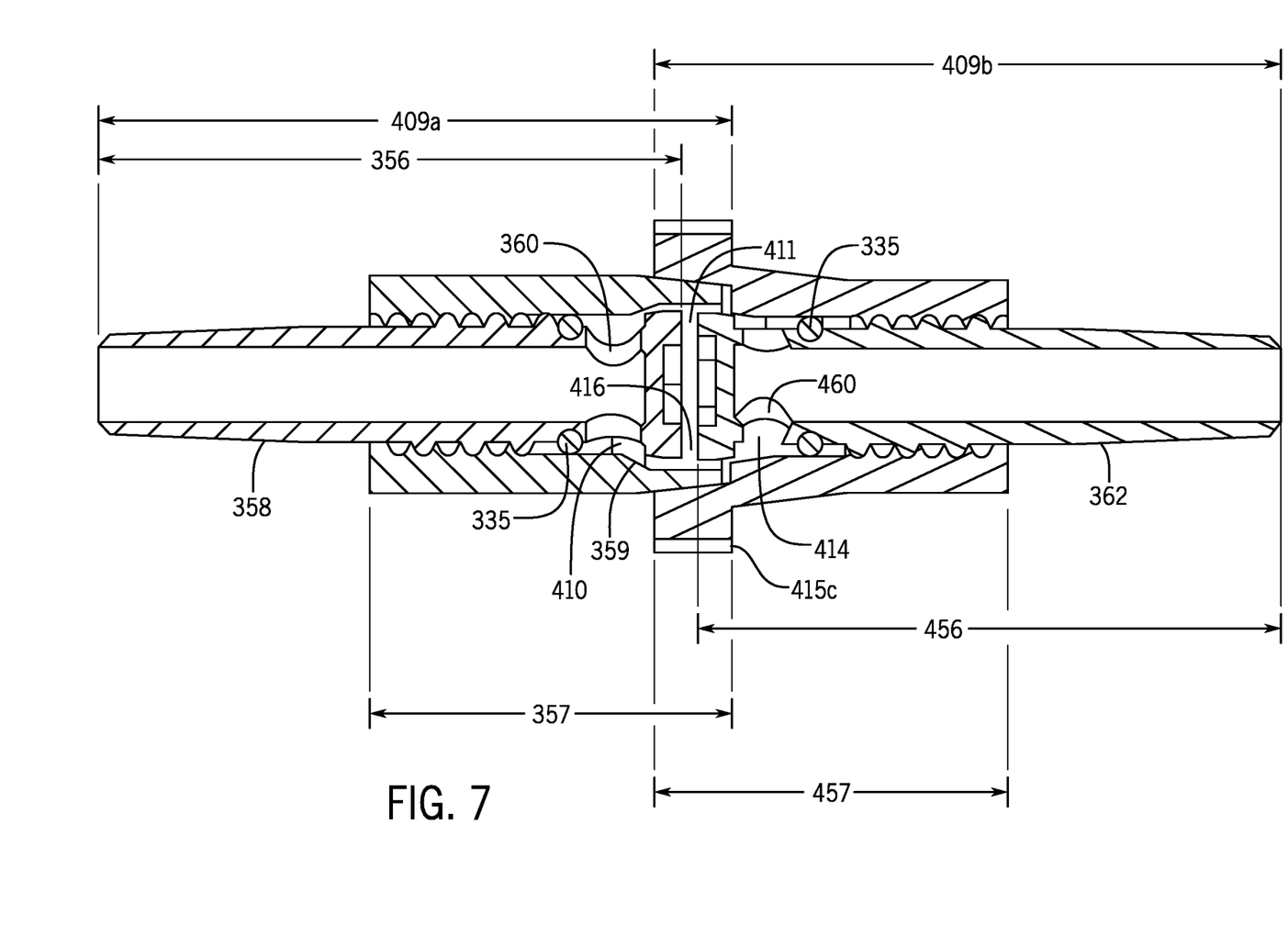
FIG. 7 is a longitudinal cross section view of the connector of FIGS. 6A-6B in which fluid communication is open between the sub-housings, according to an exemplary embodiment.

Referring to FIG. 7, once the chamber 416 and corresponding surfaces 411a, 361, 461 (FIG. 6B) have been sterilized, fluid communication may be opened between chambers 410 and 416. Sub-housing 409a may be shifted to an open configuration by rotating the socket segment 356 and connector segment 357 relative to each other. Rotation may induce translational motion of the channel 358 and end 361 towards the opening 411 relative to the small diameter portion 359 of the connector portion 357. The translational motion may open the seal between the end 361 and the small diameter portion 359. Fluid from the sub-housing 409a may flow from within the channel 358 through the orifice 360 into the chamber 410 past the small diameter portion 359 and into the sterilization chamber 416. Sub-housing 409b may likewise be shifted to an open configuration by rotating the socket segment 456 and connector segment 457 relative to each other. Rotation may induce translational motion of the channel 362 and end 461 towards the opening 415 relative to the small diameter portion 459 of the connector portion 457. The translational motion may open the seal between the end 461 and the small diameter portion 459. Fluid from the sterilization chamber 416 may flow through the small diameter portion 359 into the chamber 414 and into the orifice 460 of the channel 362.

Figure 8:
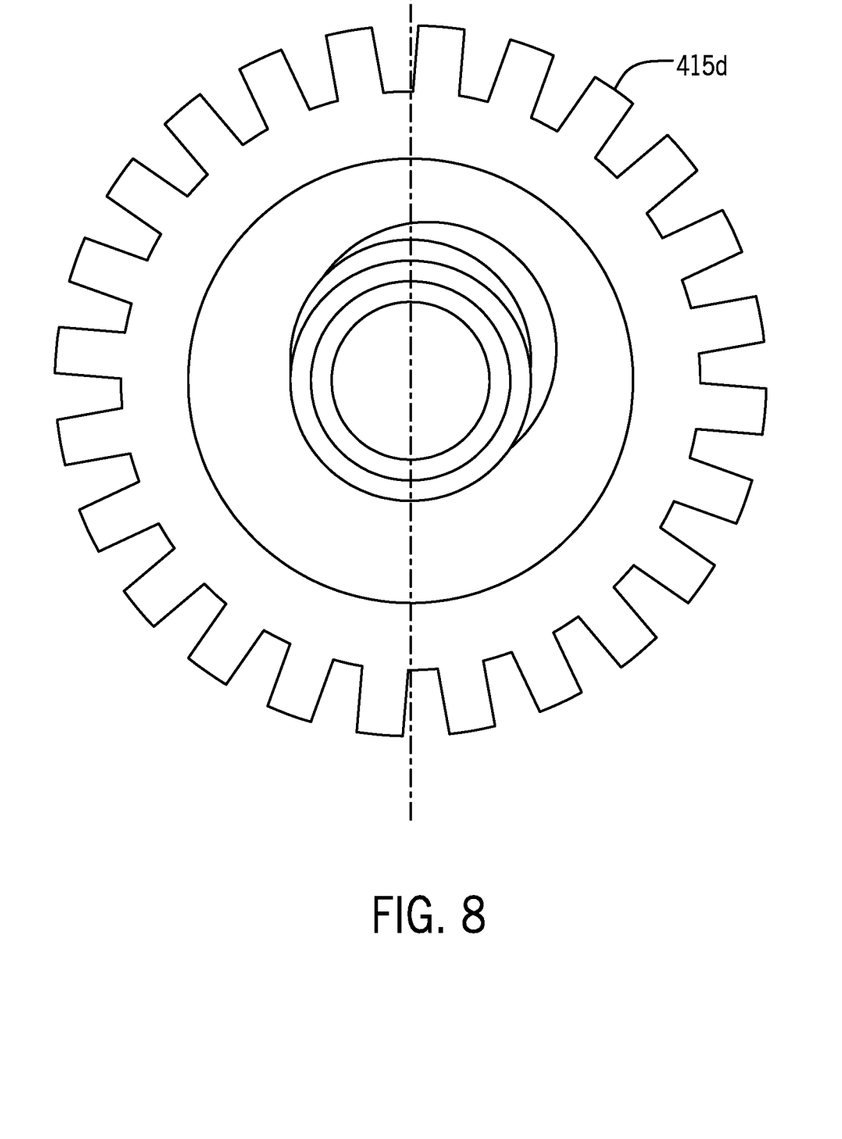
FIG. 8 is a lateral cross section view of a connector portion of the connector of FIGS. 6A, 6B, and 7, according to an exemplary embodiment.

In one embodiment, the socket portions 356, 456 may incorporate O-rings 335 disposed between outer threads 358a, 458a and the chambers 410, 414 to prevent leakage of fluid from chambers 410, 414 into the space between the socket portions 356, 456 and the connector portions 357, 457. In one embodiment, shifting the connector 350 into the open configuration via rotation of socket portions 356 and 456 relative to the connector portions 357 and 457 may be induced simultaneously by fixing the socket portions 356 and 456 in place and rotating the connector portion 457. The engagement (friction fit, interference fit, Luer fit, threaded fit, etc.) between the connector segments 357 and 457 may induce connector segment 357 to rotate along with segment 457. The outer surface 415c (FIG. 7) of the connector portion 457 may comprise an outer diameter larger than the rest of the connector portion 457. The outer surface 415c may also comprise gears 415d, as shown in FIG. 8, and may be rotated by a device having complementary gears. In one embodiment, the device providing the sterilization energy source 300 (FIG. 4) may comprise a mold configured to receive the connector 350, engage the sub-housings 409a and 409b, apply the sterilization energy source, hold the socket portions 356 and 456 in place, and shift both sub-housings 409a and 409b into open configurations simultaneously by rotating the outer surface 415c while holding the socket portions 356 and 456 in place.

Without limiting the foregoing description, in accordance with one aspect of the subject matter herein, there is provided a tube connector for a fluid circuit system comprising a housing. A first opening is configured to receive a first length of tubing in communication with a first chamber. A second opening is configured for communicating with the first chamber when the tube connector is in an open configuration but not in a closed configuration. A third opening is configured to receive a second length of tubing in communication with a second chamber. A fourth opening is configured for communicating with the second chamber when the tube connector is in the open configuration but not in the closed configuration. The second opening and the fourth opening are configured to engage each other to form a third chamber.

In accordance with a second aspect which may be used or combined with the immediately preceding aspect, the housing comprises a first sub-housing comprising the first opening, the second opening, and the first chamber. A second sub-housing comprises the third opening, the fourth opening, and the second chamber. At least a portion of the first and/or second sub-housings comprises a material comprising at least one of cyclic olefin copolymer (COC), poly (methyl methacrylate), polymethylpentene, and quartz glass.

In accordance with a third aspect which may be used or combined with the immediately preceding aspect, the first and second sub-housings each comprises a connector portion and a socket portion, and the tube connector is configured to shift from a closed configuration to an open configuration when the connector portions are rotated relative to the socket portions.

In accordance with a fourth aspect which may be used or combined with any of the preceding aspects, the tube connector is configured to shift from a closed configuration to an open configuration when the second or fourth opening is translationally shifted relative to the first or third opening.

In accordance with a fifth aspect which may be used or combined with any of the preceding aspects, the tube connector is configured to shift from a closed configuration to an open configuration when the first and/or second chamber is translationally shifted relative to the third chamber.

In accordance with a sixth aspect which may be used or combined with any of the preceding aspects, the second opening and the fourth opening are configured to engage each other in at least one of a friction fit, an interference fit, a Luer fit, and a threaded fit to form the third chamber.

In accordance with a seventh aspect which may be used or combined with any of the preceding aspects, the connector portion of the first or second sub-housings further comprises a geared outer surface, which rotation is configured to simultaneously rotate both connector portions relative to both socket portions when the socket portions are fixed in place.

In accordance with an eighth aspect, there is provided a method of sterilely connecting two fluid pathways. Provided is a first connector comprising a first chamber and a first open end and configured to connect to a first fluid pathway. The first chamber is configured to communicate with the first fluid pathway and the first open end when the first connector is in an open configuration but not in a closed configuration. Provided is a second connector comprising a second chamber and a second open end and configured to connect to a second fluid pathway. The second chamber is configured to communicate with the second fluid pathway and the second open end when the second connector is in an open configuration but not in a closed configuration. The first open end and the second open end are configured for engagement to form a third chamber. The third chamber is configured to communicate with the first chamber when the first connector is in the open configuration but not in the closed configuration and communicate with the second chamber when the second connector is in the open configuration but not in the closed configuration. The first open end and the second open end forming the third chamber comprises a first material at least partially permeable to a sterilization energy source for sterilizing contents of the third chamber. A first portion of the first connector surrounding the first chamber and a second portion of the second connector surrounding the second chamber comprise a second material less permeable to the sterilization energy source. Applying the sterilization energy source to the third chamber upon engagement of the first and second open ends when the first and second connectors are in the closed configuration and subsequently opening the first and second connectors to the open configuration allows sterile fluid from the first chamber to cross the third chamber into the second chamber while maintaining sterility.

In accordance with a ninth aspect which may be used or combined with the immediately preceding aspect, the sterilization energy source comprises a UVC emitter and the first material comprises at least one of cyclic olefin copolymer, poly(methyl methacrylate), polymethylpentene, and quartz glass. Otherwise, the sterilization energy source comprises at least one of heat, steam, ebeam, and gamma rays and the second material comprises polyurethane and/or silica aerogel.

In accordance with a tenth aspect, which may be used or combined with any of the eighth or ninth aspects, the first and second connectors each comprises a connector portion and a socket portion. The first connector is configured to shift from the closed configuration to the open configuration when the connector portion of the first connector is rotated relative to the socket portion of the first connector. The second connector is configured to shift from the closed configuration to the open configuration when the connector portion of the second connector is rotated relative to the socket portion of the second connector.

In accordance with an eleventh aspect which may be used or combined with any of the eighth through tenth aspects, the first or second connector is configured to shift from the closed configuration to the open configuration when the first or second open end is translationally shifted relative to the first or second fluid pathway.

In accordance with a twelfth aspect which may be used or combined with the any of the eighth through eleventh aspects, the first or second connector is configured to shift from the closed configuration to the open configuration when the first or second chamber is translationally shifted relative to the third chamber; or when the first or second chamber is translationally shifted relative to the first or second fluid pathway.

In accordance with a thirteenth aspect which may be used or combined with any of the eighth through twelfth aspects, the first and second open ends are configured to engage each other in at least one of a friction fit, an interference fit, a Luer fit, and a threaded fit to form the third chamber.

In accordance with a fourteenth aspect which may be used or combined with any of the twelfth and thirteenth aspects, the first and second connectors each comprises a connector portion and a socket portion. The first or second chamber is translationally shifted relative to the third chamber or to the first or second fluid pathway by rotating the connector portion of the first connector relative to the socket portion of the first connector and by rotating the connector portion of the second connector relative to the socket portion of the second connector.

In accordance with a fifteenth aspect, there is provided a sterile tube connector for a fluid circuit system comprising a housing. A first opening is configured to receive a first length of tubing in communication with a first chamber. A second opening is configured for communicating with the first chamber when the tube connector is in an open configuration but not in a closed configuration. The second opening is configured to reversibly engage a third opening to form a second chamber. The third opening is configured for communicating with a second length of tubing. A first portion of the housing forming the first opening comprises a material at least partially permeable to a sterilization energy source for sterilizing contents of the second chamber.

In accordance with a sixteenth aspect, which may be used or combined with the fifteenth aspect, a second portion of the housing forming the first opening comprises a material less permeable to the sterilization energy source In accordance with a seventeenth aspect which may be used or combined with any of the fifteenth and sixteenth aspects, the material comprises at least one of cyclic olefin copolymer, poly(methyl methacrylate), polymethylpentene, and quartz glass, and the sterilization energy source comprises UVC.

In accordance with an eighteenth aspect which may be used or combined with any of the sixteenth and seventeenth aspects, the material of the second portion comprises polyurethane and/or silica aerogel and the sterilization energy source comprises at least one of heat, steam, ebeam, and gamma rays.

In accordance with a nineteenth aspect, which may be used or combined with any of the fifteenth through eighteenth aspects, the housing further comprises a connector portion and a socket portion, and the tube connector is configured to shift from the closed configuration to the open configuration when the connector portion is rotated relative to the socket portion.

In accordance with a twentieth aspect which may be used or combined with any of the fifteenth through nineteenth aspects, the tube connector is configured to shift from the closed configuration to the open configuration when a linear force is applied to the tube connector in a direction parallel to the first length of tubing.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A tube connector for a fluid circuit system moveable between a closed configuration and an open configuration comprising: a housing comprising: a first sub-housing having a first opening configured to receive a first length of tubing in communication with a first chamber and a second opening configured for communicating with the first chamber when the tube connector is in the open configuration but not in the closed configuration; a second sub-housing having a third opening configured to receive a second length of tubing in communication with a second chamber and a fourth opening configured for communicating with the second chamber when the tube connector is in the open configuration but not in the closed configuration; each of the first and second sub-housings having a connector segment and a socket segment configured to directly secure one of the respective lengths of tubing thereto, with the socket segment being movable relative to the connector segment for the first sub-housing to move the tube connector between the closed and open configurations, and the socket segment being immovably fixed to the connector segment for the second sub-housing, wherein the second opening and the fourth opening are configured to engage each other to form a third chamber that communicates with the first chamber and the second chamber when the tube connector is in the open configuration but not when in the closed configuration.

2. The tube connector of claim 1, wherein at least a portion of the first and/or second sub-housings comprises a material comprising at least one of cyclic olefin copolymer (COC), poly(methyl methacrylate), polymethylpentene, and quartz glass.

3. The tube connector of claim 1, wherein the tube connector is configured to shift from a closed configuration to an open configuration when the second or fourth opening is translationally shifted relative to the first or third opening.

4. The tube connector of claim 1, wherein the tube connector is configured to shift from a closed configuration to an open configuration when the first and/or second chamber is translationally shifted relative to the third chamber.

5. The tube connector of claim 1, wherein the second opening and the fourth opening are configured to engage each other in at least one of a friction fit, an interference fit, a Luer fit, and a threaded fit to form the third chamber.

6. A sterile tube connector for a fluid circuit system moveable between a closed configuration and an open configuration comprising a housing comprising: a first sub-housing having a first opening configured to receive a first length of tubing in communication with a first chamber and a second opening configured for communicating with the first chamber when the tube connector is in the open configuration but not in the closed configuration; a second sub-housing having a third opening configured to receive a second length of tubing in communication with a second chamber; wherein the second opening is configured to reversibly engage the third opening to form a second chamber; each of the first and second sub-housings having a connector segment and a socket segment configured to directly secure one of the respective lengths of tubing thereto, with the socket segment being movable relative to the connector segment for the first sub-housing to move the tube connector between the closed and open configurations and the socket segment being immovably fixed to the connector segment for the second sub-housing, wherein a first portion of the housing forming the first opening comprises a material at least partially permeable to a sterilization energy source for sterilizing contents of the second chamber.

7. The sterile tube connector of claim 6, wherein a second portion of the housing forming the first opening comprises a material less permeable to the sterilization energy source.

8. The sterile tube connector of claim 6, wherein the material comprises at least one of cyclic olefin copolymer, poly(methyl methacrylate), polymethylpentene, and quartz glass, and the sterilization energy source comprises UV-C light.

9. The sterile tube connector of claim 7, wherein the material of the second portion comprises polyurethane and/or silica aerogel and the sterilization energy source comprises at least one of heat, steam, electron beam, and gamma rays.

10. The sterile tube connector of claim 6, wherein the tube connector is configured to shift from the closed configuration to the open configuration when a linear force is applied to the tube connector in a direction parallel to the first length of tubing.

11. The tube connector of claim 1 wherein the socket segment of one of the first and second sub-housings has a stopper associated therewith for selective engagement with a valve associated with the connector segment of its respective sub-housing, the stopper being mounted to a compressible member and having a tapered side wall, and the valve comprising a surface defining an aperture, the tapered side wall of the stopper being spaced from the surface defining the aperture to permit flow through the valve when in the open configuration and to engage the surface defining the aperture to prevent flow through the valve when in the closed configuration.

12. The sterile tube connector of claim 6 wherein the socket segment of one of the first and second sub-housings has a stopper associated therewith for selective engagement with a valve associated with the connector segment of its respective sub-housing, the stopper being mounted to a compressible member and having a tapered side wall, and the valve comprising a surface defining an aperture, the tapered side wall of the stopper being spaced from the surface defining the aperture to permit flow through the valve when in the open configuration and to engage the surface defining the aperture to prevent flow through the valve when in the closed configuration.

* * * * *